US009851246B2

(12) United States Patent
Van Der Post

(10) Patent No.: US 9,851,246 B2
(45) Date of Patent: Dec. 26, 2017

(54) METHOD AND APPARATUS FOR INSPECTION AND METROLOGY

(71) Applicant: ASML NETHERLANDS B.V., Veldhoven (NL)

(72) Inventor: Sietse Thijmen Van Der Post, Amsterdam (NL)

(73) Assignee: ASML NETHERLANDS B.V., Veldhoven (NL)

(*) Notice: Subject to any disclaimer, the term of this patent is extended or adjusted under 35 U.S.C. 154(b) by 16 days.

(21) Appl. No.: 15/053,968

(22) Filed: Feb. 25, 2016

(65) Prior Publication Data
US 2016/0258810 A1    Sep. 8, 2016

(30) Foreign Application Priority Data
Mar. 5, 2015    (EP) .................... 15157799

(51) Int. Cl.
| | | |
|---|---|---|
| G01B 11/04 | (2006.01) |
| G03B 27/32 | (2006.01) |
| G03B 27/74 | (2006.01) |
| G11B 11/00 | (2006.01) |
| G01J 1/44 | (2006.01) |
| G01B 11/02 | (2006.01) |

(Continued)

(52) U.S. Cl.
CPC .............. *G01J 1/44* (2013.01); *G01B 11/02* (2013.01); *G01N 21/956* (2013.01); *G02B 21/0016* (2013.01); *G03F 7/70325* (2013.01); *G03F 7/70483* (2013.01); *G03F 7/70516* (2013.01); *G03F 7/70625* (2013.01); *G03F 7/70633* (2013.01); *G01J 2001/444* (2013.01)

(58) Field of Classification Search
CPC ...... G01B 9/04; G01B 11/02; G01B 2210/56; G01J 1/44; G02B 21/0016; G03F 7/70325; G03F 7/70483; G03F 7/70516; G03F 7/70625; G03F 7/70633; G03F 7/70641; G03F 7/70825; G03F 9/703; G11B 7/1387
USPC ........... 355/67, 68, 77; 356/237.5, 625, 635, 356/636; 359/823; 369/13.33
See application file for complete search history.

(56) References Cited

U.S. PATENT DOCUMENTS 7,791,732 B2    9/2010  Den Boef et al.
8,411,287 B2    4/2013  Smilde et al.
(Continued)

FOREIGN PATENT DOCUMENTS

| EP | 0 503 236 | 9/1992 |
| KR | 10-1192466 | 10/2012 |
| WO | 2007/132398 | 11/2007 |

OTHER PUBLICATIONS

Peng Xie et al., "Scanning interference evanescent wave lithography for sub-22 nm generations," Proc. of SPIE, vol. 8326, pp. 83260Y-1-83260Y-14 (Feb. 21, 2012).
(Continued)

*Primary Examiner* — Colin Kreutzer
(74) *Attorney, Agent, or Firm* — Pillsbury Winthrop Shaw Pittman LLP

(57) ABSTRACT

A method and apparatus for optical metrology is disclosed. There is disclosed, for example, a method involving a radiation intensity distribution for a target measured using an optical component at a gap from the target, the method including calculating a correction factor for the variation of radiation intensity of the radiation intensity distribution as a function of variation of the distance of the gap.

20 Claims, 14 Drawing Sheets

(51) Int. Cl.
*G03F 7/20* (2006.01)
*G02B 21/00* (2006.01)
*G01N 21/956* (2006.01)

(56) References Cited

U.S. PATENT DOCUMENTS

| | | |
|---|---|---|
| 8,605,257 B2 | 12/2013 | Scheible et al. |
| 8,731,882 B2 | 5/2014 | Van Beurden |
| 9,081,303 B2 | 7/2015 | Cramer et al. |
| 2006/0066855 A1 | 3/2006 | Boef et al. |
| 2008/0089208 A1 | 4/2008 | Verschuren |
| 2009/0040906 A1* | 2/2009 | Hong .............. G11B 7/0908 369/112.23 |
| 2009/0316979 A1 | 12/2009 | Gidon |
| 2011/0027704 A1 | 2/2011 | Cramer et al. |
| 2011/0043791 A1 | 2/2011 | Smilde et al. |
| 2012/0044470 A1 | 2/2012 | Smilde et al. |
| 2015/0198524 A1 | 7/2015 | Sapiens et al. |

OTHER PUBLICATIONS

International Search Report and Written Opinion dated Jul. 8, 2016 in corresponding International Patent Application No. PCT/EP2016/053306.

Wan-Chin Kim et al., "Effects of optical variables in immersion lens-based near-field optics," Optics Express, vol. 16, No. 18, pp. 13933-13948 (Sep. 1, 2008).

* cited by examiner

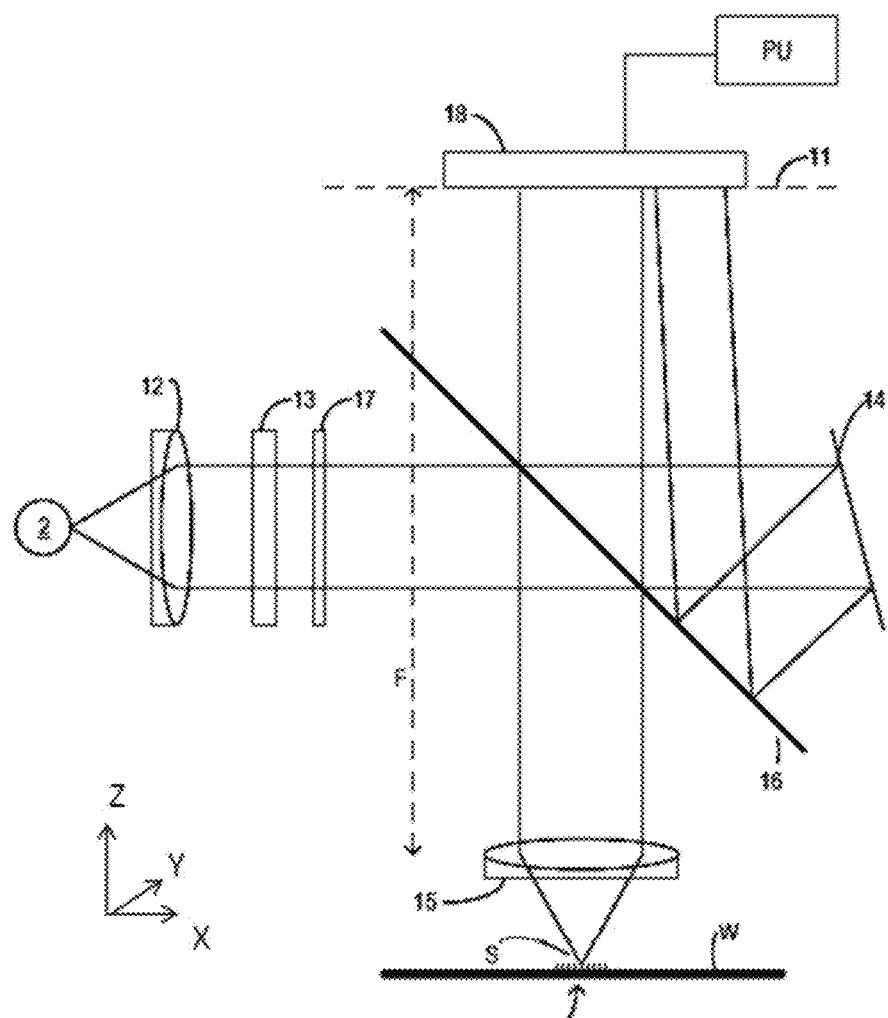
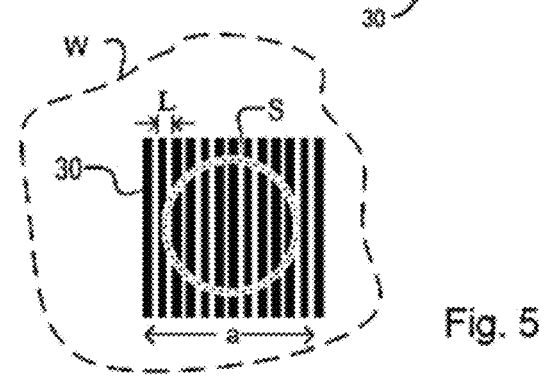
Fig. 4
Fig. 5

METHOD AND APPARATUS FOR
INSPECTION AND METROLOGY

This application claims the benefit of priority of European Patent Application No. 15157799.6, filed on Mar. 5, 2015, which is incorporated herein in its entirety by reference.

FIELD

The present description relates to a method and apparatus for correction of error in measured radiation distribution captured from a metrology target.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithographic process, the patterned substrate is inspected and one or more parameters of the patterned substrate are measured. The one or more parameters may include, for example, the overlay error between successive layers formed in or on the patterned substrate and/or critical linewidth of developed photosensitive resist. This measurement may be performed on a target of the product substrate itself and/or on a dedicated metrology target provided on the substrate. There are various techniques for making measurements of the microscopic structures formed in lithographic processes, including the use of a scanning electron microscope and/or various specialized tools.

A fast and non-invasive form of specialized inspection tool is a scatterometer in which a beam of radiation is directed onto a target on the surface of the substrate and properties of the scattered or reflected beam are measured. By comparing one or more properties of the beam before and after it has been reflected or scattered by the substrate, one or more properties of the substrate can be determined. Two main types of scatterometer are known. A spectroscopic scatterometer directs a broadband radiation beam onto the substrate and measures the spectrum (intensity as a function of wavelength) of the radiation scattered into a particular narrow angular range. An angularly resolved scatterometer uses a monochromatic radiation beam and measures the intensity of the scattered radiation as a function of angle.

A particular application of scatterometry is in the measurement of feature asymmetry within a periodic target. This can be used as a measure of overlay error, for example, but other applications are also known. In an angle resolved scatterometer, asymmetry can be measured by comparing opposite parts of the diffraction spectrum (for example, comparing the $-1$st and $+1^{st}$ orders in the diffraction spectrum of a periodic grating). This can be done simply in angle-resolved scatterometry, as is described for example in U.S. patent application publication US2006-066855.

SUMMARY

With reduction of the physical dimensions in lithographic processing, there is demand to, for example, increase measurement accuracy and/or reduce the space occupied by targets dedicated to metrology. Image based scatterometry measurements have been devised to allow the use of smaller targets, by taking separate images of the target using $-1^{st}$ and $+1^{st}$ order radiation in turn. Examples of this image based technique are described in published U.S. patent application publication nos. US2011-0027704, US2011-0043791 and US2012-0044470, which are incorporated herein in their entirety by reference.

Demand for further reduction in target size and for improved accuracy continues, however, and existing techniques suffer from various constraints that make it difficult to maintain accuracy and/or reduce the size of the targets. Another way to improve on inspection and measurement techniques is to use a solid immersion lens (SIL) as the optical element nearest the substrate surface. The extreme proximity of the SIL with the substrate surface (e.g., target surface) results in a very high effective numerical aperture (NA) larger than 1. Using an incoherent or coherent radiation source with this SIL allows a very small target to be inspected.

To take advantage of the increasing numerical aperture, the gap between the SIL and the substrate should be set to a desired value. For example, the gap may be within the range of 10-50 nm to have the SIL in effective optical contact with the substrate. An example optical gap measuring method and apparatus can involve detecting cross components of polarization in the high numerical aperture element. The cross polarized signal is then recorded by a detector and can be used as an input parameter into a gap control process. In another example, the gap may be controlled by reference to reflected laser radiation intensity. As will be appreciated, other methods and apparatus may be used to arrive at a signal representative of the gap (e.g., representative of its size or of its variation from a nominal size).

Irrespective of any detecting method, the gap between the SIL (or other component) and the substrate (or other surface) should be established, and maintained at, a desired gap distance or distance range, typically by an associated actuator and control system. This is because the measurement data (e.g., intensity data, image, etc.) derived from the radiation redirected by the target, and obtained using the SIL (or other component), depends on the gap, and so any parameter of interest (e.g., height of a part of the target pattern, width of a part of the target pattern, thickness of one or more various layers of the target pattern, etc.) will depend on the gap distance because the radiation redirected from the substrate is evanescently coupled to the SIL.

But, regardless of the control mechanism used to establish, and maintain, the desired gap, a residual dynamic error is generally present in the gap, i.e., there is a dynamic error in the gap distance from the desired or expected gap distance. And, it has been discovered that even a small variation in the gap distance in the absolute sense may cause unacceptably large error in the determination of one or more parameters of interest derived from the measurement data. Accordingly, it is desired to provide, for example, one or more methods and apparatus to correct measurement data obtained using a SIL (or other component) for a residual error in the gap between the SIL and the substrate, and/or derive a parameter of interest using corrected measurement data.

In an aspect, there is provided a method to correct radiation intensity associated with a target for reconstruction of one or more parameters of interest relating to the target.

In an aspect, there is provided a method involving a radiation intensity distribution for a target measured using an optical component at a gap from the target, the method comprising: calculating a correction factor for the variation of radiation intensity of the radiation intensity distribution as a function of variation of the distance of the gap.

In an aspect, there is provided a method comprising: for a given target structure, calculating a second-order derivative tensor for dependence of radiation intensity on a gap between the target structure and an optical element; determining a statistical variance of a gap variation distribution over a measurement period; and determining a variation in radiation intensity for the target structure based on the statistical variance and the second-order derivative tensor.

In an aspect, there is provided a method comprising: for a given target structure, calculating a second-order derivative tensor for dependence of radiation intensity on a gap between the target structure and an optical element; evaluating statistical variance of a gap variation distribution for a measurement period of the target, the gap variation distribution being based on a measured gap signal; and evaluating a mean radiation intensity variation across the target structure as a function of variation of the gap based on the second-order derivative tensor and the statistical variance of the gap variation distribution.

BRIEF DESCRIPTION OF THE DRAWINGS

Embodiments will now be described, by way of example only, with reference to the accompanying drawings in which:

FIG. 4 schematically depicts an example inspection apparatus;

FIG. 5 illustrates the relationship between an illumination spot of an inspection apparatus and a metrology target;

DETAILED DESCRIPTION

Before describing embodiments in detail, it is instructive to present an example environment in which embodiments may be implemented.

Figure 1:
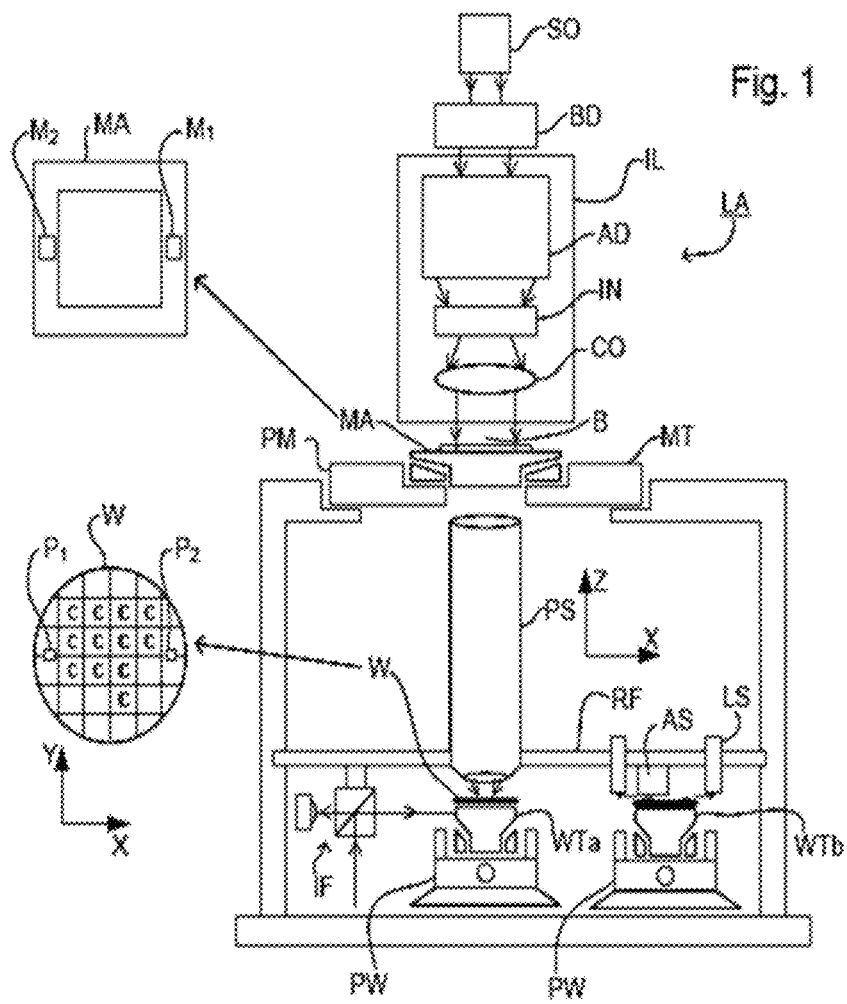
FIG. 1 schematically depicts an embodiment of a lithographic apparatus.

FIG. 1 schematically depicts a lithographic apparatus LA. The apparatus comprises:

an illumination system (illuminator) IL configured to condition a radiation beam B (e.g. UV radiation or DUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W, the projection system supported on a reference frame (RF).

The illumination system may include various types of optical components, such as refractive, reflective, magnetic, electromagnetic, electrostatic or other types of optical components, or any combination thereof, for directing, shaping, or controlling radiation.

The support structure supports the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more tables (e.g., two or more substrate tables WTa, WTb, two or more patterning device tables, a substrate table WTa and a table WTb below the projection system without a substrate that is dedicated to, for example, facilitating measurement, and/or cleaning, etc.). In such "multiple stage" machines the additional tables may be used in parallel, or preparatory steps may be carried out on one or more tables while one or more other tables are being used for exposure. For example, alignment measurements using an alignment sensor AS and/or level (height, tilt, etc.) measurements using a level sensor LS may be made.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the patterning device and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
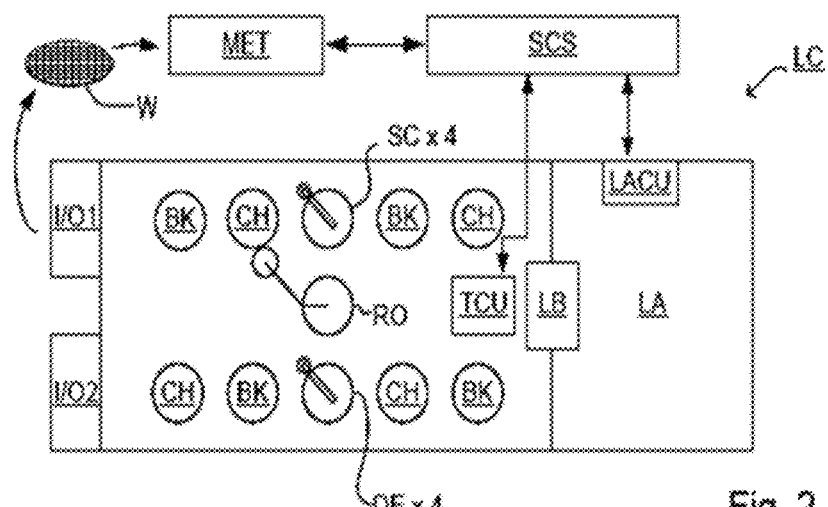
FIG. 2 schematically depicts an embodiment of a lithographic cell or cluster.

As shown in FIG. 2, the lithographic apparatus LA may form part of a lithographic cell LC, also sometimes referred to a lithocell or cluster, which also includes apparatuses to perform pre- and post-exposure processes on a substrate. Conventionally these include one or more spin coaters SC to deposit one or more resist layers, one or more developers DE to develop exposed resist, one or more chill plates CH and/or one or more bake plates BK. A substrate handler, or robot, RO picks up one or more substrates from input/output port I/O1, I/O2, moves them between the different process apparatuses and delivers them to the loading bay LB of the lithographic apparatus. These apparatuses, which are often collectively referred to as the track, are under the control of a track control unit TCU which is itself controlled by the supervisory control system SCS, which also controls the lithographic apparatus via lithography control unit LACU. Thus, the different apparatuses can be operated to maximize throughput and processing efficiency.

In order that a substrate that is exposed by the lithographic apparatus is exposed correctly and consistently, it is desirable to inspect an exposed substrate to measure one or more properties such as overlay error between subsequent layers, line thickness, critical dimension (CD), etc. Accordingly a manufacturing facility in which lithocell LC is located also typically includes a metrology system MET which receives some or all of the substrates W that have been processed in the lithocell. The metrology system MET may be part of the lithocell LC, for example it may be part of the lithographic apparatus LA.

Metrology results may be provided directly or indirectly to the supervisory control system SCS. If an error is detected, an adjustment may be made to exposure of a subsequent substrate (especially if the inspection can be done soon and fast enough that one or more other substrates of the batch are still to be exposed) and/or to subsequent exposure of the exposed substrate. Also, an already exposed substrate may be stripped and reworked to improve yield, or discarded, thereby avoiding performing further processing on a substrate known to be faulty. In a case where only some target portions of a substrate are faulty, further exposures may be performed only on those target portions which are good.

Within a metrology system MET, an inspection apparatus is used to determine one or more properties of the substrate, and in particular, how one or more properties of different substrates vary or different layers of the same substrate vary from layer to layer. The inspection apparatus may be integrated into the lithographic apparatus LA or the lithocell LC or may be a stand-alone device. To enable rapid measurement, it is desirable that the inspection apparatus measure one or more properties in the exposed resist layer immediately after the exposure. However, the latent image in the resist has a low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of a faulty substrate but may still provide useful information.

Figure 3:
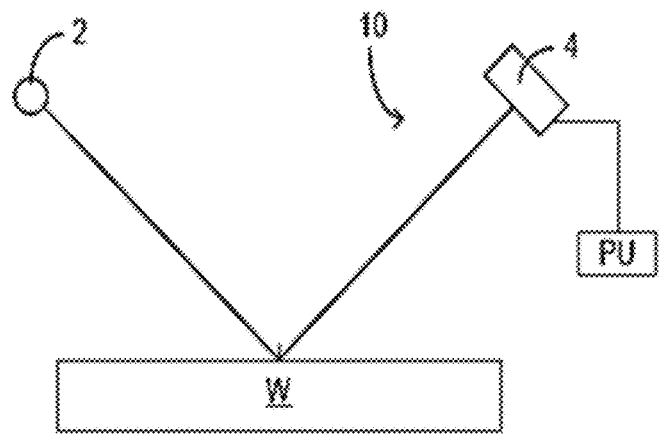
FIG. 3 schematically depicts an example inspection apparatus and metrology technique.
Figure 3:
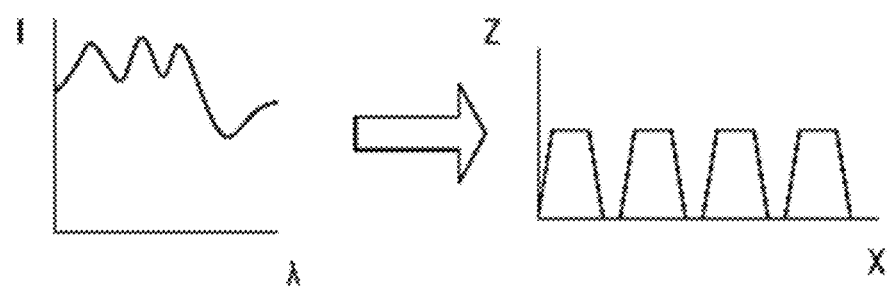

FIG. 3 depicts an example inspection apparatus (e.g., a scatterometer). It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 3. In general, for the reconstruction the general form of the structure is known and some parameters are assumed from knowledge of the process by which the structure was made, leaving only a few parameters of the structure to be determined from the measured data. Such an inspection apparatus may be configured as a normal-incidence inspection apparatus or an oblique-incidence inspection apparatus.

Another inspection apparatus that may be used is shown in FIG. 4. In this device, the radiation emitted by radiation source 2 is collimated using lens system 12 and transmitted through interference filter 13 and polarizer 17, reflected by partially reflecting surface 16 and is focused into a spot S on substrate W via an objective lens 15, which has a high numerical aperture (NA), desirably at least 0.9 or at least 0.95. An immersion inspection apparatus (using a relatively high refractive index fluid such as water) may even have a numerical aperture over 1.

As in the lithographic apparatus LA, one or more substrate tables may be provided to hold the substrate W during measurement operations. The substrate tables may be similar or identical in form to the substrate tables WTa, WTb of FIG. 1. In an example where the inspection apparatus is integrated with the lithographic apparatus, they may even be the same substrate table. Coarse and fine positioners may be provided to a second positioner PW configured to accurately position the substrate in relation to a measurement optical system. Various sensors and actuators are provided for example to acquire the position of a target of interest, and to bring it into position under the objective lens 15. Typically many measurements will be made on targets at different locations across the substrate W. The substrate support can be moved in X and Y directions to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

The radiation redirected by the substrate W then passes through partially reflecting surface 16 into a detector 18 in order to have the spectrum detected. The detector may be located in a back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector may be a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam may be used, for example, to measure the intensity of the incident radiation. To do this, when the radiation beam is incident on the partially reflecting surface 16 part of it is transmitted through the partially reflecting surface 16 as a reference beam towards a reference mirror 14. The reference beam is then projected onto a different part of the same detector 18 or alternatively on to a different detector (not shown).

One or more interference filters 13 is available to select a wavelength of interest in the range of, say, 405-790 nm or even lower, such as 200-300 nm. The interference filter may be tunable rather than comprising a set of different filters. A grating could be used instead of an interference filter. An aperture stop or spatial light modulator (not shown) may be provided in the illumination path to control the range of angle of incidence of radiation on the target.

The detector 18 may measure the intensity of redirected radiation at a single wavelength (or narrow wavelength range), the intensity separately at multiple wavelengths or integrated over a wavelength range. Furthermore, the detector may separately measure the intensity of transverse magnetic- and transverse electric-polarized radiation and/or the phase difference between the transverse magnetic- and transverse electric-polarized radiation.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may be etched into the substrate. The pattern (e.g., of bars, pillars or vias) is sensitive to chromatic aberration in the lithographic projection apparatus, particularly the projection system PS, and illumination symmetry and the presence of such aberration will manifest in a variation in the printed grating. Accordingly, the measured data of the printed grating is used to reconstruct the grating. One or more parameters of the 1-D grating, such as line width and/or shape, or one or more parameters of the 2-D grating, such as pillar or via width or length or shape, may be input to the reconstruction process, performed by processor PU, from knowledge of the printing step and/or other inspection processes.

In addition to measurement of a parameter by reconstruction, angle resolved scatterometry is useful in the measurement of asymmetry of features in product and/or resist patterns. A particular application of asymmetry measurement is for the measurement of overlay, where the target 30 comprises one set of periodic features superimposed on another. The concepts of asymmetry measurement using the instrument of FIG. 3 or FIG. 4 are described, for example, in U.S. patent application publication US2006-066855, which is incorporated herein in its entirety. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 4, where detector 18 may be an image sensor, such asymmetry in the diffraction orders appears directly as asymmetry in the pupil image recorded by detector 18. This asymmetry can be measured by digital image processing in unit PU, and calibrated against known values of overlay.

FIG. 5 illustrates a plan view of a typical target 30, and the extent of illumination spot S in the apparatus of FIG. 4. To obtain a diffraction spectrum that is free of interference from surrounding structures, the target 30, in an embodiment, is a periodic structure (e.g., grating) larger than the width (e.g., diameter) of the illumination spot S. The width of spot S may be smaller than the width and length of the target. The target in other words is 'underfilled' by the illumination, and the diffraction signal is free from interference by product features and the like outside the target itself. The illumination arrangement 2, 12, 13, 17 may be configured to provide illumination of a uniform intensity across a pupil plane of objective 15. Alternatively, by, e.g., including an aperture in the illumination path, illumination may be restricted to on axis or off axis directions.

Figure 6:
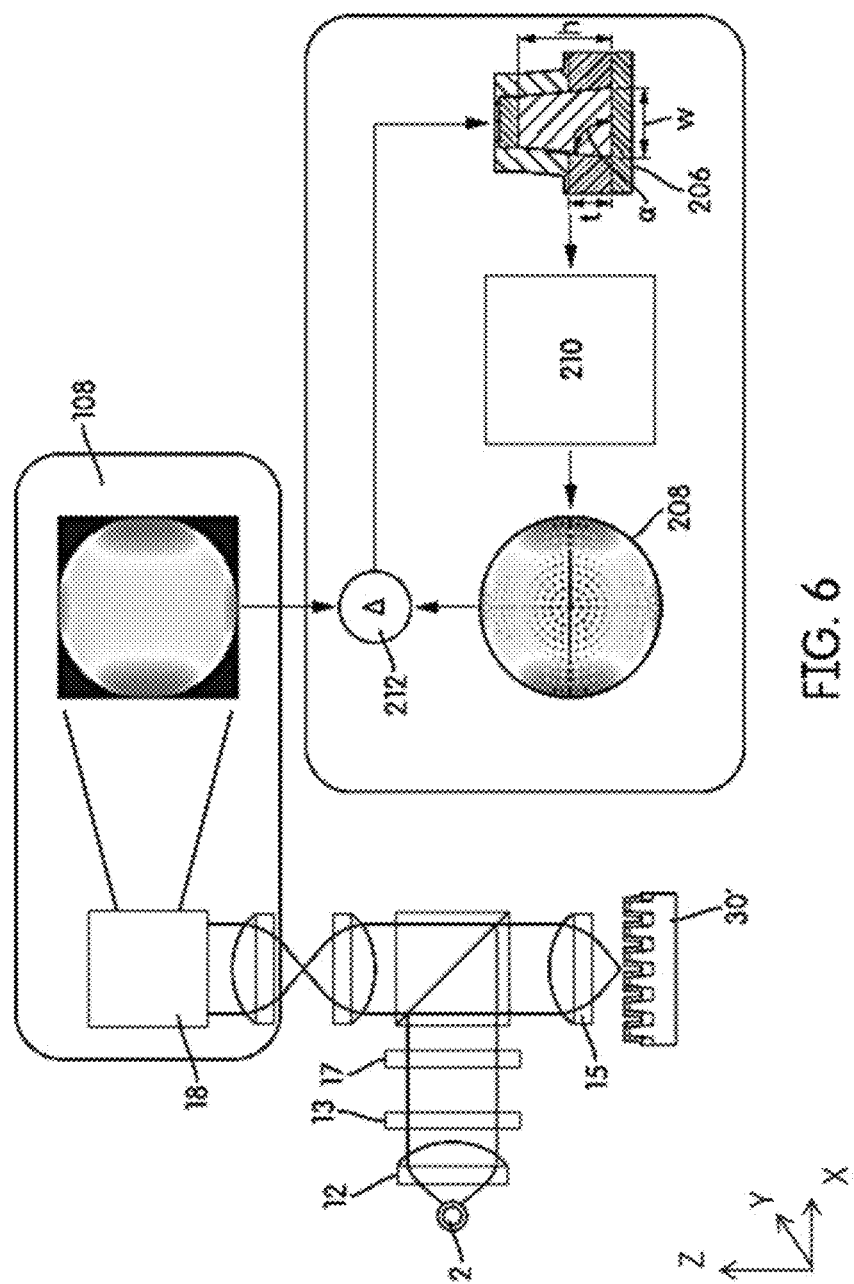
FIG. 6 schematically depicts a process of deriving a parameter of interest based on measurement data.
Figure 7:
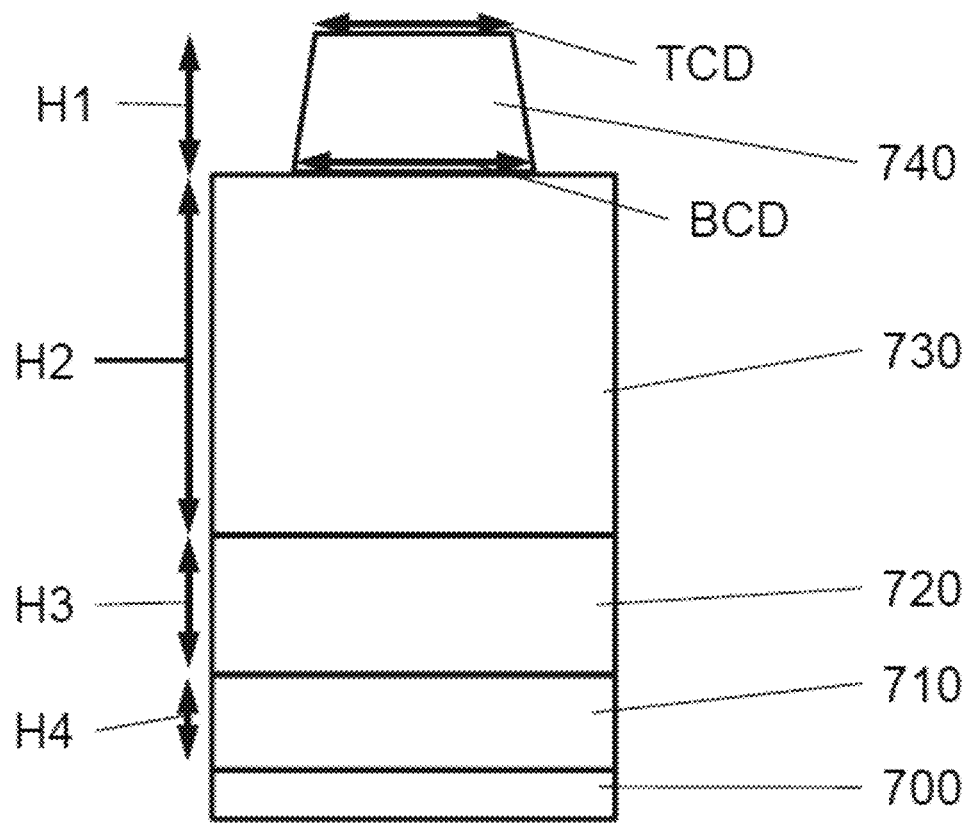
FIG. 7 depicts an example of one pitch of a target marker.

FIG. 6 schematically depicts an example process of the determination of one or more parameters of interest of a target pattern based on measurement data obtained using metrology. Radiation detected by detector 18 provides a measured radiation distribution 108 for target 30'. This measured radiation distribution 108 contains information to enable derivation of a parameter of interest such as the overlay error between successive layers formed in or on the substrate and/or critical dimension of, e.g., developed photosensitive resist. FIG. 7 depicts an example portion of a target (such as target 30, 30') and example layers of various materials making up, and associated with, the target. For example, the target may comprise a layer of silicon dioxide ($SiO_2$) 710 overlying the bare silicon substrate 700. Overlying layer 710 may be a layer of silicon nitride ($Si_3N_4$) 720, which may form a grating feature, having a layer of TEOS (tetraethyl orthosilicate) 730 overlying it. Overlying layer 730 is a further layer of silicon nitride ($Si_3N_4$) 740, which may form a further grating feature (e.g., a grating feature for measuring overlay). FIG. 7 further depicts various parameters of the target that help to define the target, e.g., the distance H1 representing the thickness of layer 710, the distance H2 representing the thickness of layer 720, the distance H3 representing the thickness of layer 730, the distance H4 representing the thickness of layer 740, top critical dimension TCD of layer 740, and bottom critical dimension BCD of layer 740. These various (and other) parameters influence the radiation distribution obtained at detector 18.

For a given target 30', a radiation distribution 208 can be computed/simulated from a parameterized model 206 of the pattern for target 30' using, for example, a numerical Maxwell solver 210. The parameterized model 206 may include one or more of the parameters identified in FIG. 7 and/or other parameters such as refractive index of one or more of the layers, a sidewall angle of one or more layers, etc. The initial values of the parameters may be those expected for the target being measured. The measured radiation distribution 108 is then compared at 212 to the computed radiation distribution 208 to determine the difference between the two. If there is a difference, the values of one or more of the parameters of the parameterized model 206 may be varied, a new computed radiation distribution 208 calculated and compared against the measured radiation distribution 108 until there is sufficient match between the measured radiation distribution 108 and the computed radiation distribution 208. At that point, the values of the parameters of the parameterized model 206 provide a good or best match of the geometry of the actual target 30'. One of those parameters of the parameterized model (e.g., CD) may be used by the user for evaluating the lithographic process. Additionally or alternatively, a parameter of interest may be derived from one or more of the values of the parameterized model.

But, there is demand to reduce the space occupied by metrology targets.

For example, there is a desire to reduce the width of 'scribe lanes' between target portions C on the substrate, where metrology targets have conventionally been located. Additionally or alternatively, there is a desire, for example, to include metrology targets within the device patterns themselves, to allow more accurate monitoring and correction of variations in parameters such as CD and/or overlay. To this end, alternative methods of diffraction based metrology have been devised more recently. For example, in image-based metrology, two images of the target are made, each using different selected orders of the diffraction spectrum. Comparing the two images, one can obtain asymmetry information. By selecting parts of the images, one can separate the target signal from its surroundings. The targets can be made smaller, and need not be square, so that several can be included within the same illumination spot. Examples of this technique are described in U.S. patent application publications US2011-0027704, US2011-0043791, and US2012-0044470.

In addition to or alternatively to reducing the space occupied by metrology targets, there is demand to improve the nature of the measurements themselves, such as their accuracy. For example, there is a desire to, for example, obtain higher sensitivity of measurement. Additionally or alternatively, there is a desire to, for example, obtain better decoupling between various parameters in the reconstruction described above. For example, it is desired to obtain better values for each of the specific parameters of interest, by reducing or eliminating the effect of measurements associated with one parameter of interest influencing another parameter of interest.

As the demand for size reduction and/or accuracy continues, existing techniques may meet some technical limitations. For example, some methods desire to capture at least the $\pm 1^{st}$ diffraction orders. Taking into account the numerical aperture of the objective 15, this constrains the pitch (L) of a periodic structure of the target. To improve sensitivity and/or to reduce target size, one can consider using shorter wavelengths λ. Further, the target cannot be too small otherwise it will not have enough features to be considered as a periodic structure. Consequently, overlay, as an example, is measured using periodic structures features (e.g., lines) having dimensions far bigger than those of the product (e.g., device) layout, making overlay measurement less reliable. Ideally the feature line and pitch should have similar dimensions to the product features.

Figure 8:
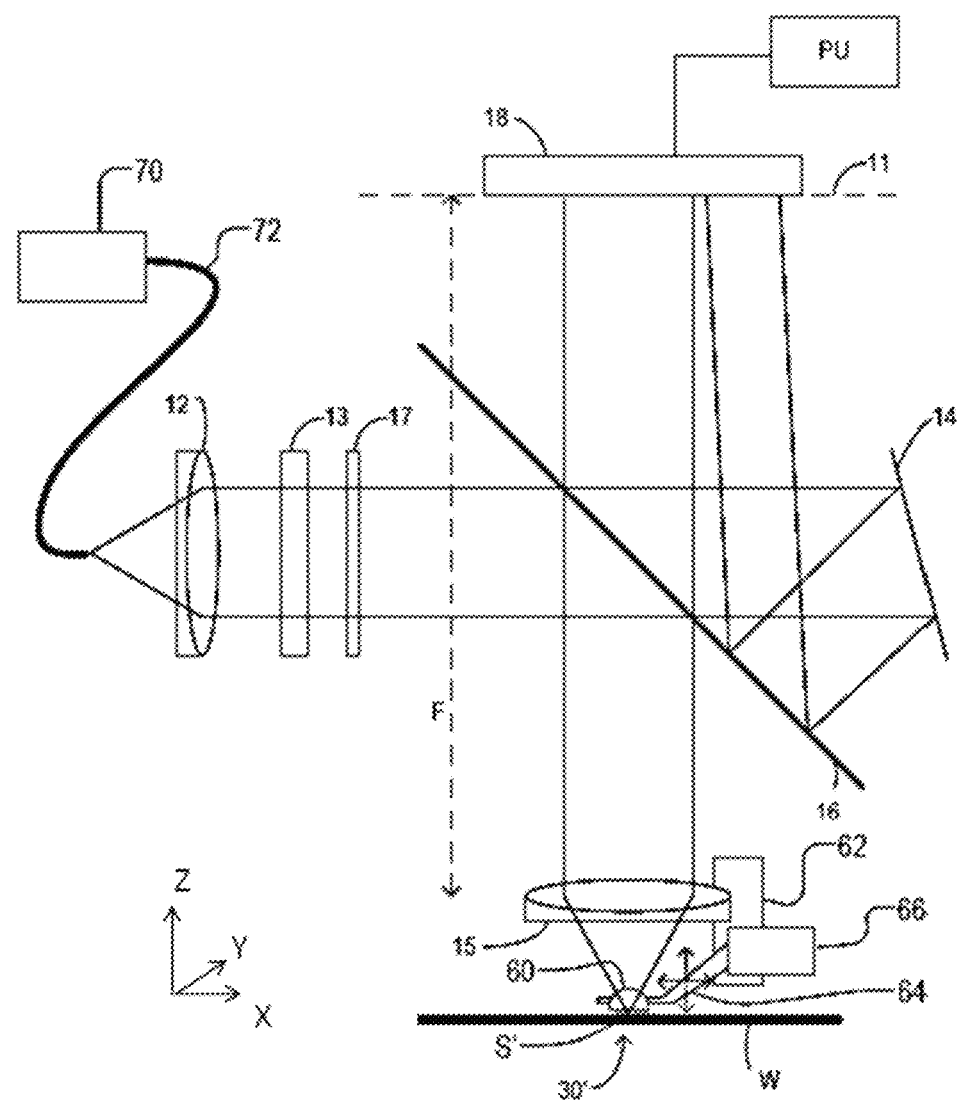
FIG. 8 depicts an example inspection apparatus comprising a solid immersion lens (SIL)

FIG. 8 shows an inspection apparatus in which improvement of the nature of the measurements themselves (e.g., accuracy) and/or reduction of target size may be realized. In FIG. 8, a spot S' (which may be smaller than convention if, for example, a smaller target is desired) can be applied to a target 30' (which may be smaller than convention, e.g., features of smaller pitch, if, for example, a smaller target is desired). Like reference numerals refer to like components throughout the figures.

Comparing the apparatus of FIG. 8 with that of FIG. 4, a first difference is the provision of an additional lens element 60 close to the target 30'. This additional lens is a miniature solid immersion lens (SIL), with a width (e.g., diameter) only on the order of a millimeter, for example in the range of 1 mm to 5 mm, for example about 2 mm. The SIL comprises, in an example, a hemisphere of material that receives rays of radiation at substantially normal incidence to its surface. In an embodiment, the SIL may be a different shape such as a super-hemisphere. In an embodiment, the SIL is made up of a material of refractive index n, such as glass, fused quartz, a combination of materials, etc. Within the SIL material, the numerical aperture (NA) of the original rays is multiplied by n. The received rays come to focus at about the center of the hemisphere or super-hemisphere and form a spot that is smaller by a factor of n compared to what would have been in the absence of the SIL. For example, a typical glass hemisphere having n=2 will reduce the width of the focused spot by a factor of 2.

Immersion of optical elements in liquid has been used to increase resolution in microscopy and photolithography. The solid immersion lens may achieve similar gains without the inconvenience/problems of liquid immersion. However, to ensure that the increased NA does indeed increase the resolution of the system, the bottom of the SIL must either be in contact with the target 30 or positioned extremely closely to it. This restricts its practical applications.

A so-called micro-SIL may also be used. The width (e.g., diameter) of such a SIL is many times smaller, for example about 2 microns in width instead of about 2 millimeters. In an example where SIL 60 in the FIG. 8 apparatus is a micro-SIL, it may have a width (e.g., diameter) less than or equal to 10 μm, potentially less than or equal to 5 μm.

Whether a miniature or micro-SIL 60 is used, it can be attached to a movable support so that controlling the alignment and proximity to the substrate is much simpler than in the case of a lens with bigger width. For example, the SIL 60 in FIG. 8 is mounted to a frame 62. In an embodiment, frame 62 is movable. An actuator may be provided to move frame 62. In an embodiment, the frame 62 supports the objective 15. Accordingly, in an embodiment, the frame 62 may move both the objective 15 and the SIL 60 together. In an embodiment, the actuator for the frame 62 may be configured to move the frame 62 (and the SIL 60) in substantially the Z direction. In an embodiment, the actuator for the frame 62 may be configured to move the frame 62 (and the SIL 60) around the X axis and/or Y axis. In an embodiment, the SIL 60 is in relative fixed position relative to the frame 62. This may be referred to a single stage arrangement, where the objective 15 and SIL 60 are fixed relative to each and are moved by the actuator of frame 62. In such a case, a benefit may be that the SIL can be mechanically positioned in the focus of the objective.

As noted above, the SIL 60 in FIG. 8 is mounted to a frame 62, which in an embodiment supports objective 15. Of course, the SIL 60 may be mounted on a separate frame from that supporting objective 15. In an embodiment, the SIL 60 is connected to a frame (e.g., frame 62) via an arm 64 and actuator 66. Actuator 66 may be, for example, piezoelectric in operation or voice coil actuated. The arrangement where the SIL 60 has an actuator to cause relative movement between a movable objective 15 and the SIL 60 may be referred to as a dual stage arrangement. In a dual stage, certain functionalities may be separated. For example, the (relatively large) objective stage comprises the relatively heavy objective and can have relatively large motion range. In an embodiment, the objective stage may move only substantially in the Z-direction (substantially normal to the surface). Further, it can have a certain bandwidth (e.g., ~100 Hz) sufficient for relatively long displacement ranges, but perhaps not sufficient (e.g., too low) for suppression of small surface disturbances. The (relatively small) SIL stage comprises the relatively light SIL and can have a relatively small motion range. In an embodiment, the SIL stage may move in at least 3 degrees of freedom, e.g., in the Z-direction and around the X-axis and/or the Y-axis, to position the SIL substantially parallel to the surface. Further, it can have a certain bandwidth (e.g., sufficiently high) to suppress small surface disturbances (e.g., ~1-5 nm). The SIL stage may not have a mechanical range sufficient to cover the desired full travel range. So, the SIL stage can be used to position the SIL at about 10-50 nm above the surface, while the objective stage can position the objective at focus with respect to the surface.

Actuator 66 may operate in combination with one or more other actuators positioning the objective as a whole in relation to the target. In relation to the coarse and fine positioners mentioned above, for example, the actuator 66 may be regarded as an ultra-fine positioner. The servo control loops of these different positioners can be integrated with one another. The components 62, 64 and 66, together with the substrate table and positioners (mentioned above but not shown in FIG. 8), form a support apparatus for positioning the SIL and the target T in close proximity to one another. AS noted above, in principle, SIL 60 could be mounted rigidly to the frame 62, and/or may be of larger width. The separate arm and actuator allows easier control of the very small gap, as discussed in more detail below.

Inclusion of the SIL 60 opens the possibility of focusing to a much smaller spot S'. The SIL works by capturing the near-field radiation from the target, and to this end it is positioned substantially closer than one wavelength (λ) of radiation from the target structure, generally closer than a half wavelength, for example around λ/20. The closer the distance, the stronger will be the coupling of near-field signals into the instrument. The gap between the SIL 60 and target 30' may therefore be less than 100 nm, for example between 10 nm and 50 nm. Because the NA of the inspection apparatus is effectively increased, the sensitivity and parameter de-correlation is enhanced such that the pitch of the target periodic structure may be reduced closer to product dimensions.

In examples where a micro-SIL would be used, incoherent radiation of the type conventionally used in, for example, a scatterometer cannot be focused to a micron-sized spot as small as the micro-SIL. Accordingly, in such an embodiment or in an embodiment using a macro-SIL (i.e., one larger than a micro-SIL) the radiation source 2 may be changed to a coherent source. Therefore a laser source 70 is coupled to illumination optics 12, etc. via an optical fiber 72. The limit on the spot size on the substrate is set by the numerical aperture of the focusing lens system and the laser wavelength. As an additional benefit of using spatially coherent radiation, the instrument with laser radiation source 70 can be used to perform different types of scatterometry or measurement. For example, coherent Fourier scatterometry (CFS) may be used to measure the target.

As highlighted above, a small gap should be maintained between the SIL and the target. As also highlighted above, known techniques for controlling the gap have limitations, particularly when a variety of different target structures and materials are to be inspected.

But, even if the control for gap is improved, a residual dynamic error of the control system will be difficult, if not impossible, to eliminate. That is, regardless of the control mechanism, the actual value of a gap (e.g., a value in the range of 10-50 nm, e.g., 20, 25, 30, or 35 nm) may vary because of various factors such as vibrations in the apparatus, movement around the apparatus, vibration of the floor on which the apparatus sits, variability in Van der Waals forces, and so forth.

Figure 9:
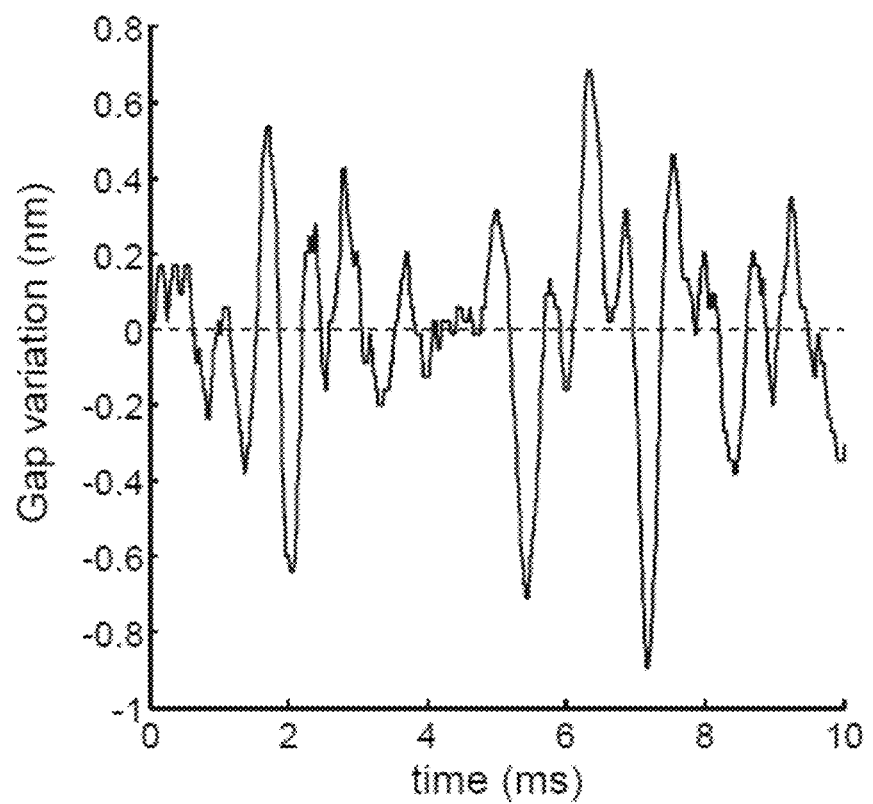
FIG. 9 depicts an example of simulated values of a deviation of a gap from its nominal value in time (gap variation)

FIG. 9 shows an example deviation from the nominal value of the gap versus time for the acquisition of measurement data using a SIL at a gap in the range of 10-50 nm. That is, the variable plotted in FIG. 9 is the change from a desired or expected gap value, rather than a measurement of the absolute gap distance, and this data is for a SIL controlled to be at the certain nominal value. As can be seen in FIG. 9, while the absolute value of the variability can be relatively small, the variation is quite significant and moreover, some values may be relatively high compared to the nominal value. Accordingly, it may be incorrect to assume when deriving one or more parameters of interest from a radiation distribution measured using a SIL that the gap assumes a single value over the acquisition time and that the error is not significant enough. So, assuming a single value for the gap distance over an acquisition period of measurement data may decrease precision of the one or more reconstructed parameters of interest. Accordingly, it is desirable to apply a correction to the measurement data, and/or one or more parameters of interest derived from the measurement data, to account for the variability in gap distance.

So, to make this kind of correction, there should be a measure of the gap distance variability. The gap variation may be determined/measured using any available gap related signal. In an embodiment, the control signal used to control the gap may be used as a proxy for the gap variation. Such a signal may be sufficient to measure the gap variation distribution in real time for a particular data collection. Further, as known in the art, a gap error signal (GES) may be used and obtained/measured using any of the techniques known in the art, now or hereafter. Further, to enable correction of a particular set of measurement data, information about (e.g., values of) the gap variation related to the measurement data should be available. For example, there may be provided information about (e.g., values of) the gap variation for at least part, if not all, of the acquisition time of the measurement data. For example, there may be provided information about (e.g., values of) the gap variation that is obtained prior to a time of obtaining all or part of the measurement data, e.g., dynamic behavior obtained without actually measuring it during acquisition.

Figure 10A:
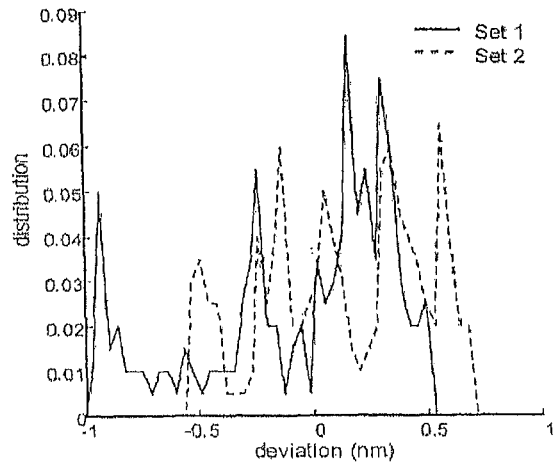
FIGS. 10A-10C depict example simulated gap variation distributions associated with two sets of data over respective different acquisition times.
Figure 10B:
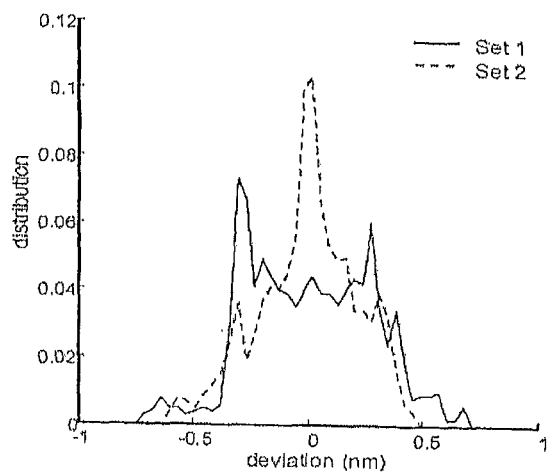
Figure 10C:
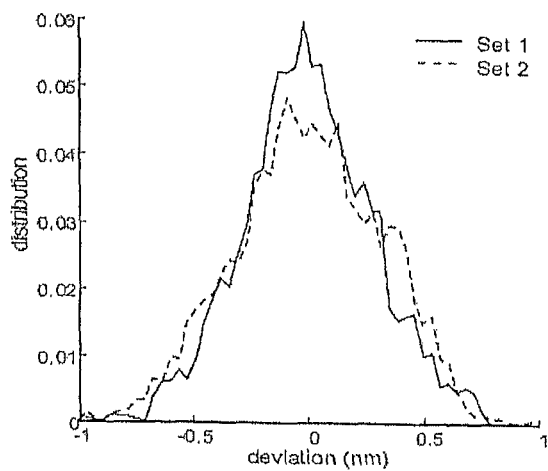
Figure 11A:
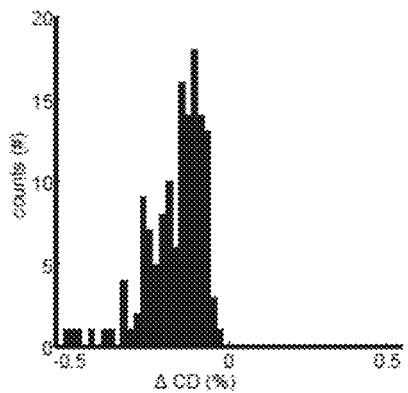
FIG. 11A depicts an example frequency of occurrence of various simulated values of variation of top CD for a set of simulated gap distributions used for reconstruction of a target pattern.
Figure 11B:
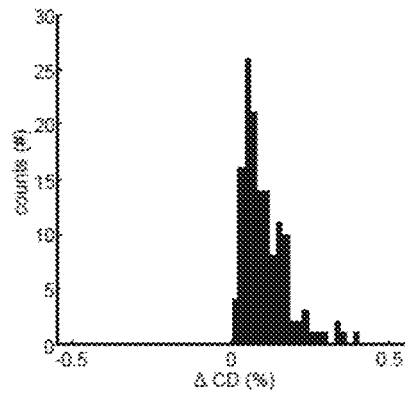
FIG. 11B depicts an example frequency of occurrence of various simulated values of variation of bottom CD for a set of simulated gap distributions used for reconstruction of a target pattern.
Figure 11C:
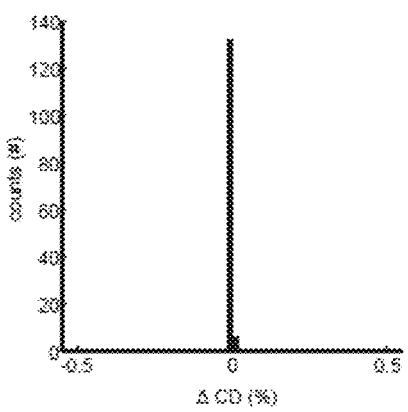
FIG. 11C depicts an example frequency of occurrence of various simulated values of variation of height of a grating for a set of simulated gap distributions used for reconstruction of a target pattern.
Figure 11D:
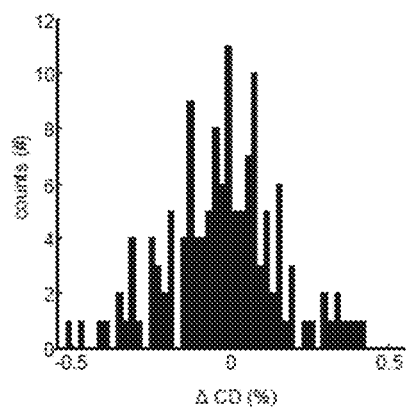
FIG. 11D depicts an example frequency of occurrence of various simulated values of variation of gap distance for a set of simulated gap distributions used for reconstruction of a target pattern.

FIGS. 10A-10C show graphs for distribution of gap variation over three different time intervals (2 ms, 10 ms, and 60 ms, respectively) for two example sets of data collections. The distributions depict the probability in the y-axis for a particular variation in gap in the x-axis during the particular acquisition time. As can be seen, the gap variation distribution may differ for different data collections. The gap variation distribution, thus, depends not only on the dynamic behavior of the SIL at and during the particular acquisition time, but also on the acquisition time over which the behavior is measured. Accordingly, the measurement of the same target under the same general conditions (e.g., same nominal gap distance, measurement radiation wavelength, etc.) can yield different sets of measurement data, and accordingly different values of one or more derived parameters of interest, due to the variability in gap distance not only during the acquisition time but the variability of that variation between collections of the data.

As discussed above, the intensity of radiation coupled through the SIL is sensitive to variation in the gap. Thus, even small residual errors in the gap, e.g., on the order of 1 nm (as seen in FIG. 9) may induce reconstruction errors that are more than desired tolerance levels. For example, FIGS. 11A-11D depict the computed (via, for example, a simulation) variation of top CD, bottom CD, height of a grating feature of the target (e.g., H1 in FIG. 7), and mean gap (respectively) for simulated measurement of a target, such as the target of FIG. 7. In this example, the radiation intensity distribution from the target was determined a plurality of times, each simulation having its own respective gap distribution for a particular acquisition time (e.g., 2 ms). From those radiation intensity distributions, the top CD, bottom CD, and height of the grating feature were derived and then their variation from the actual CD was determined (since this is simulated data the true CD is known). Further, the mean gap is the mean of the gap distance over the acquisition time and its variation from the nominal gap distance was calculated. So, the graphs show, in the x axis, the percentage of variation of the particular parameter (i.e., from its true or nominal value) and, in the y-axis, the number of occurrences of that particular variation in the set of simulated measurements. While the height of the grating feature shows little variance in its CD variation (and the variation is virtually nil, i.e., the heights as determined from the simulated intensity distributions mostly matched the height as used in the simulation) and the variation in the mean gap is fairly evenly distributed, it can be seen unexpectedly that there is quite a significant non-uniformity in the distribution of the variations of top CD and bottom CD and moreover that the distributions were skewed from zero.

Accordingly, in an embodiment, a method and apparatus are proposed to correct radiation intensity used for the reconstruction of one or more parameters of interest relating to the target. So, to do so, a correction is provided that can be applied to a measured or calculated intensity distribution to arrive at a corrected intensity distribution, which can be used to derive one or more parameters of interest.

To arrive at the correction, a model of an intensity distribution to grating-model parameters can be established. In particular, a model of variation in the intensity distribution to variation of one or more grating-model parameters can be established. For example, the relation between a variation in grating-model parameters $\Delta P_i$ and an intensity variation $\Delta I$ of a pixel measured in the pupil can be written as the following Taylor expansion:

$$\Delta I(\Delta P) = \sum_{i=1}^{n} J_i \Delta P_i + \frac{1}{2} \sum_{i,j=1}^{n} H_{ij} \Delta P_i \Delta P_j + \frac{1}{6} \sum_{i,j,k=1}^{n} T_{ijk} \Delta P_i \Delta P_j \Delta P_k + \ldots \quad \text{Eq. (1)}$$

where J, H, and T represent the first, second and third-order derivative tensors of the pixel intensities to the parameters respectively, and given by:

$$J_i = \frac{\partial I}{\partial P_i} \quad \text{Eq. (2)}$$

$$H_{ij} = \frac{\partial I}{\partial P_i \partial P_j} \quad \text{Eq. (3)}$$

$$T_{ijk} = \frac{\partial I}{\partial P_i \partial P_j \partial P_k} \quad \text{Eq. (4)}$$

If it is assumed that only the gap variation $\Delta A$ is non-zero (i.e., a perfect model except for the variation of the gap), the average intensity change due to variation in the gap can be expressed as:

$$\overline{\Delta I}(\Delta A) = \mu_1 J_a + \frac{1}{2} \mu_2 H_{aa} + \frac{1}{6} \mu_3 T_{aaa} + \ldots \quad \text{Eq. (5)}$$

where $\mu_i$ represents the i-th mathematical moment of the gap variation distribution (i.e., distribution shape parameters) and the index a represents the index of the gap parameter. So, the moments are given by:

$$\mu_1 = \frac{1}{N} \sum_{i=1}^{N} X_i \quad \text{Eq. (6)}$$

$$\mu_n = \frac{1}{N} \sum_{i=1}^{N} (X_i - \mu_1)^n \quad \text{Eq. (7)}$$

where X represents the gap distance variation. Thus, the first moment $\mu_1$ is the mean of the gap variation distribution, the second moment $\mu_2$ is the variance of the gap variation distribution, the third moment $\mu_3$ is the skewness of the gap variation distribution, the fourth moment $\mu_4$ is the kurtosis of the gap variation distribution, and so forth. Accordingly, variation in intensity change can be calculated as a function of various moments of gap variation distribution.

Figure 12A:
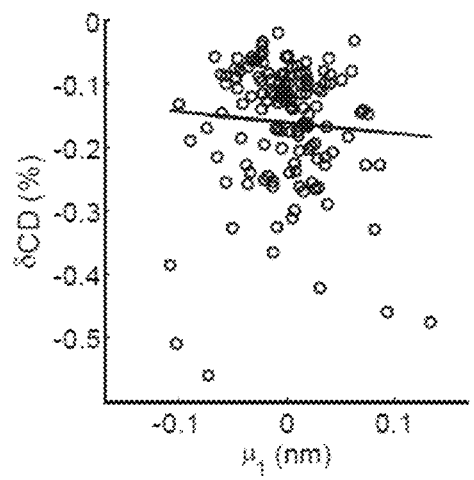
FIGS. 12A-12D depict the dependence of variation in CD (for top CD) to various simulated values of a mathematical moment of simulated gap distributions for various different types of mathematical moments of gap distributions.
Figure 12B:
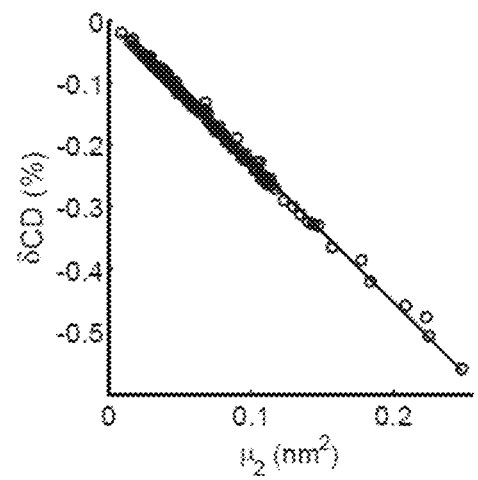
Figure 12C:
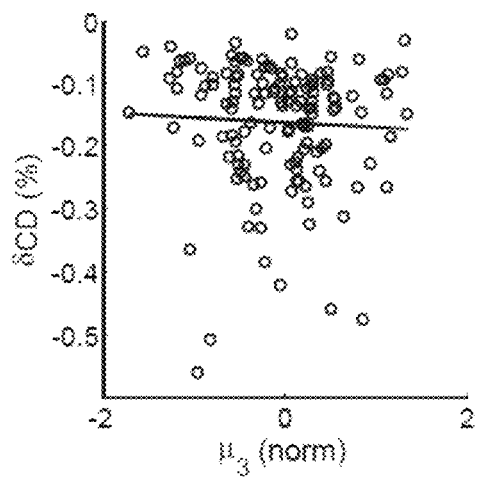
Figure 12D:
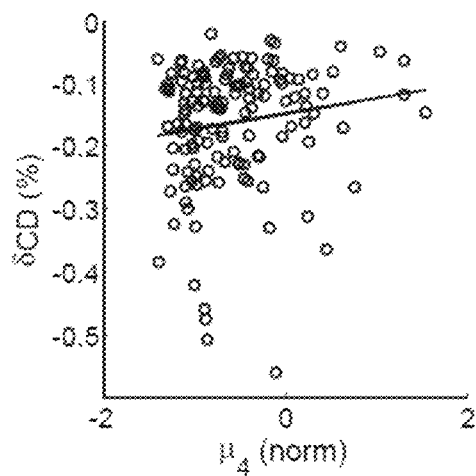

Now, the variation in each of various parameters of interest (which parameters are reconstructed from an intensity distribution) can be evaluated against various moments of the gap distribution. For example, FIGS. 12A-12D depict the computed variation in top CD ("y") computed from a set of simulated gap variation distributions for various values of the first four mathematical moments ("x") of the gap variation distributions. FIG. 12A shows results for the first moment (mean), FIG. 12B shows results for the second moment (variance), FIG. 12C shows results for the third moment (skewness) and FIG. 12D shows results for the fourth moment (kurtosis). FIGS. 12C and 12D show normalized values of skewness and kurtosis. On reviewing FIGS. 12A-12D, it is evident from FIG. 12B that the top CD is strongly correlated with the second moment (i.e., variance) of the gap variation distribution for a set of gap variation distributions.

Figure 13A:
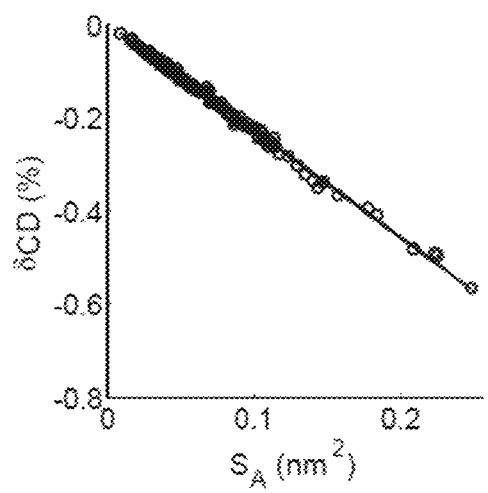
FIGS. 13A-13G depict the dependence of variation in CD for various parameters related to the target pattern with variance (second mathematical moment) of simulated gap distributions.
Figure 13B:
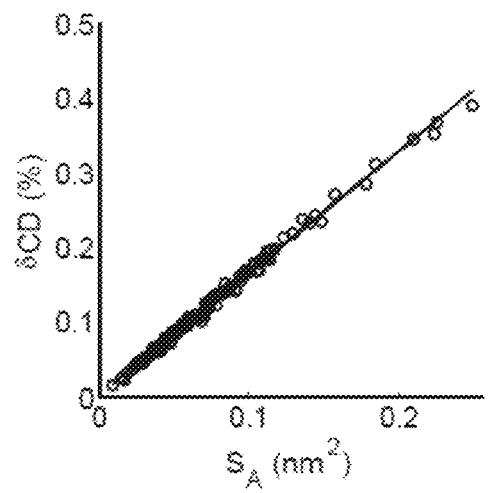
Figure 13C:
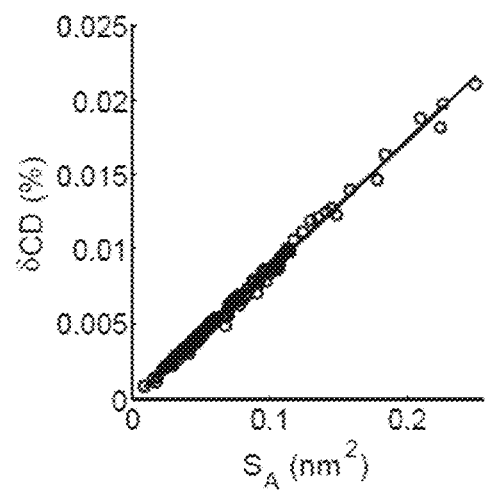
Figure 13D:
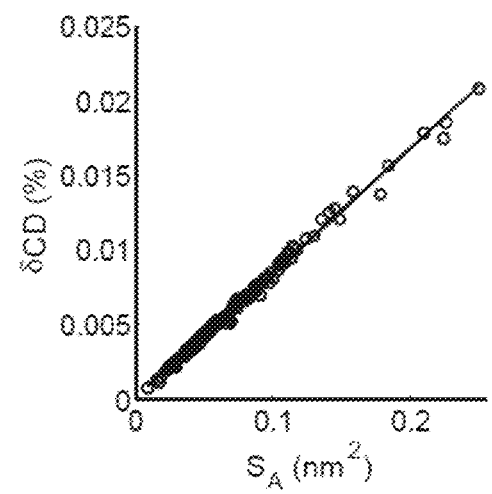
Figure 13E:
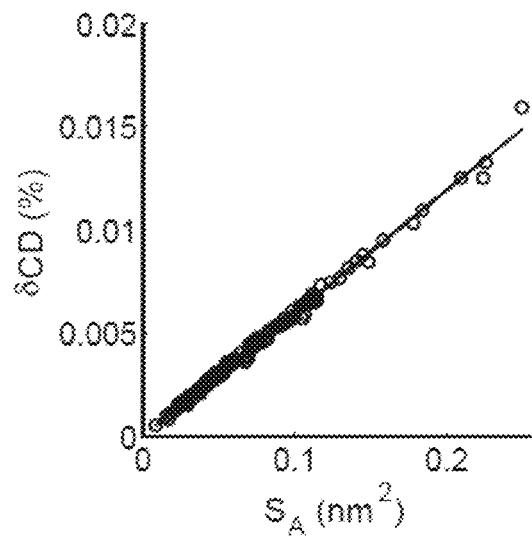
Figure 13F:
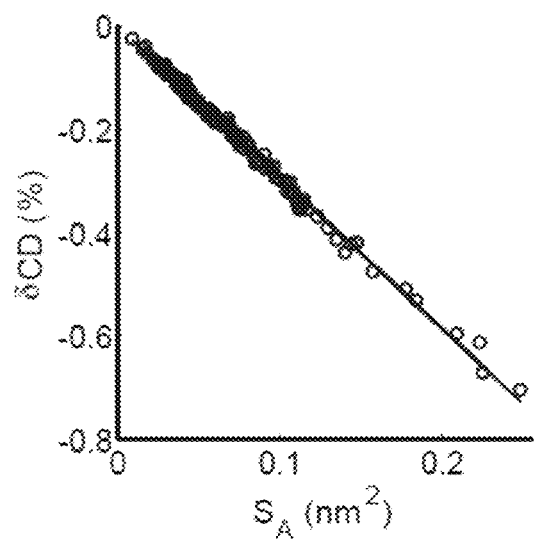
Figure 13G:
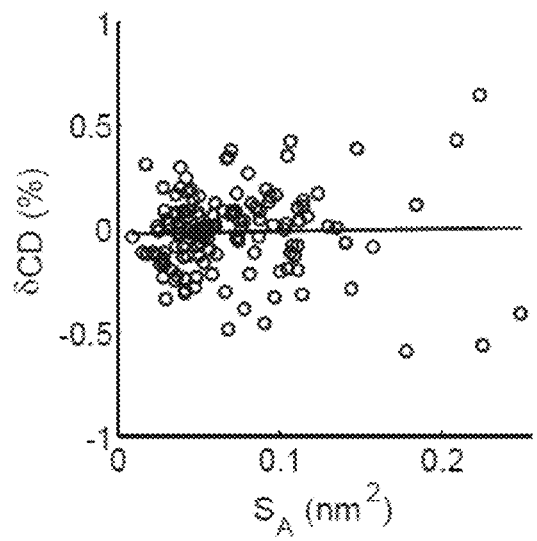

FIGS. 13A-13G depict the computed variation of various parameters of interest ("y") computed from a set of simulated gap variation distributions for various values of the second moment (variance) ("x") of the gap variation distributions. FIG. 13A shows results for top CD, FIG. 13B shows results for bottom CD, FIG. 13C shows results for H1 (see FIG. 7), FIG. 13D shows results for H2 (see FIG. 7), FIG. 13E shows results for H3 (see FIG. 7), FIG. 13F shows results for H4 (see FIG. 7), and FIG. 13G shows results for the mean gap. The strong (linear) correlation between the variance of gap variation distribution and the various parameters of interest as shown in FIGS. 13A-F is clearly evident.

It may be concluded, based on FIGS. 12A-C and 13A-F that: (1) the first-order intensity change (linear in the mean of the gap variation distribution) is fully absorbed by the gap parameter itself; (2) the second-order intensity change (linear in the variance of the gap variation distribution) causes a variation in one or more other parameters of interest that is linear to the variance; and (3) the third-order intensity change (linear in the skewness of the gap variation distribution) or higher order intensity change may be too small to have a significant effect on one or more other parameters of interest (although for greater accuracy it may be included in the calculations).

Therefore, to remove undesired variation of a parameter of interest due to the dynamic residual error of the gap, it may be possible to calculate a correction factor of the $H_{aa}$ elements of the second-order derivative tensor based on the applicable model (i.e., the particular nominal gap value at measurement, the particular target structure (e.g., dimensions, refractive indices of layers of the target, etc.) being measured, the particular radiation wavelength and/or polarization used, etc.). In an embodiment, the second-order derivative tensor is calculated across the pupil, i.e., comprises a map or matrix of the various points (pixels) in the pupil. Then, in combination with the variance $\mu_2$ of the gap variation distribution calculated for a particular measurement data acquisition, an intensity distribution may be corrected with, e.g., low computational cost.

Thus, it may, therefore, be sufficient to calculate the $H_{aa}$ elements of the second-order derivative tensor (e.g., the Hessian matrix) based on the model discussed above only once to correct for the dynamic residual error of the gap when reconstructing one or more parameters of interest based on a measured radiation distribution obtained from a target. Further, the variance $\mu_2$ can be obtained in near real-time during data acquisition by using a control signal representing the gap distance or its variation. So, using the second-order derivative tensor calculated for the particular target and measurement conditions and the variance calculated from a particular measurement data acquisition, an intensity distribution can, thus, be corrected at a low computation cost.

Figure 14:
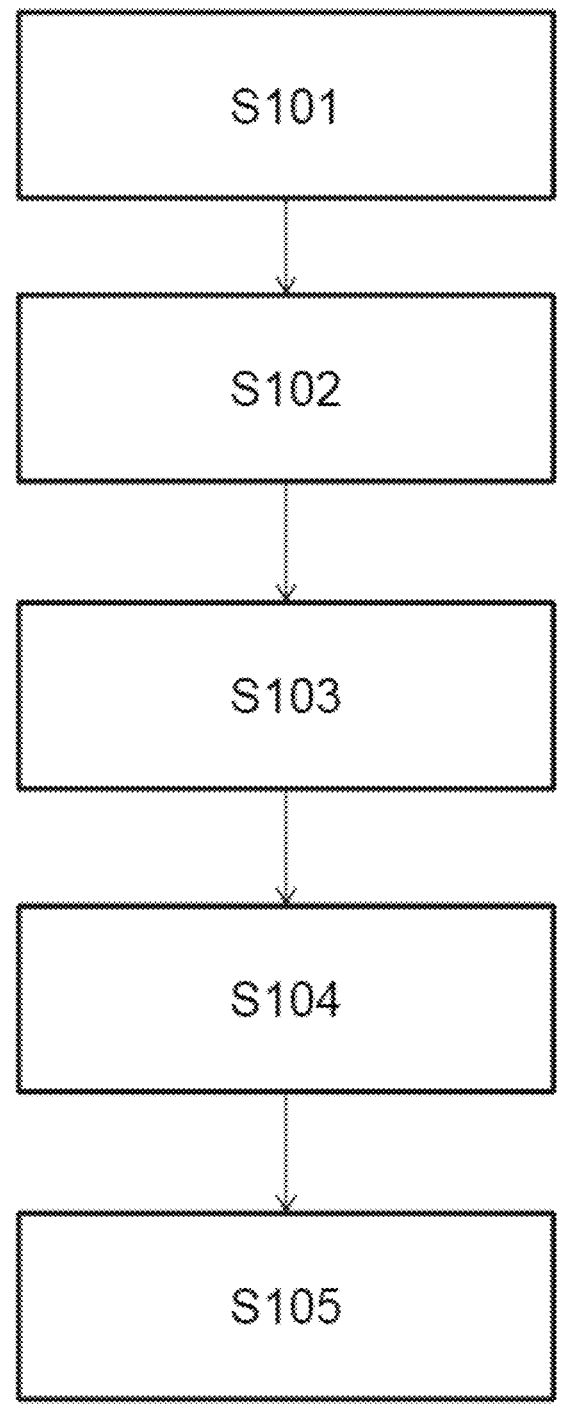
FIG. 14 depicts a flow diagram of a process to derive one or more parameters of interest of a target pattern based on measured data obtained using a SIL.

FIG. 14 depicts a flow diagram of a method of correcting an intensity distribution according to an embodiment. At step S101, for a given target structure and measurement conditions (e.g., nominal gap value, radiation wavelength and/or polarization), the second-order derivative tensor (e.g., a Hessian matrix) of the dependence of radiation intensity on gap variation between the target and an optical element is calculated. The second-order derivative tensor can be calculated using, e.g., an appropriate simulation or other mathematical calculation using the given target structure and measurement conditions.

For example, the derivative tensor can be calculated as follows, first for the first-order derivative tensor. A model is provided for the target (e.g., a grating), parametrized by a set of parameters P=(p1, p2, p3, . . . ). A solver (e.g., a Maxwell solver) can calculate the pupil intensity distribution that would be measured for this target with the given parameters. The intensity distribution in the pupil is denoted by I(kx,ky), with (kx,ky) being the coordinates of the pupil. So, a nominal pupil $I_{nom}$(kx,ky|p1, p2, . . . ) can be calculated for the set of nominal parameters $P_{nom}$=(p1, p2, . . . ) and for every parameter, the intensity can be calculated in case that parameter is varied a small amount. For the first parameter that would be $dI_1$(kx,ky|p1+delta, p2, . . . ) for the parameter values P=(p1+delta, p2, . . . ), with a small delta. The first-order derivative (the Jacobian) of the first parameter is then given by $J_1$(kx,ky)=($dI_1$(kx,ky|p1+delta, p2, . . . )−$I_{nom}$(kx,ky|p1, p2, . . . ))/delta. The procedure to calculate the second or higher order derivative tensor is similar, except that now also higher order cross-terms are included, for example the pupil $dI_{12}$(kx,ky|p1+delta, p2+delta, p3, . . . ) is calculated for the contribution $H_{12}$(kx,ky)=($dI_{12}$(kx,ky)−$I_{nom}$(kx,ky))/delta^2, etc.

At step S102, statistical variance of a gap variation distribution for an acquisition period is determined. The gap variation distribution is based on a measured or other gap signal. As has been discussed, the gap signal may be any signal indicative of the absolute gap or a variation in gap. For example, the measured gap signal may be a control signal received from the controller that is used for positioning the SIL relative to the target surface.

At step S103, a variation in radiation intensity (e.g., mean variation) at points (pixels) across the pupil due to the gap variation is calculated based the second-order derivative tensor for the particular points and the statistical variance of the gap variation distribution.

At step S104, a correction may be applied to an intensity distribution associated with the target based on the calculated variation in radiation intensity. For example, the calculated radiation intensity variation at the various spatial positions may be subtracted/added to the measured radiation intensity at the corresponding various spatial positions obtained using the SIL to arrive at a corrected measured radiation intensity distribution. So, for example, the radiation intensity distribution 108 may be corrected to arrive at a corrected radiation intensity distribution, which corrected radiation intensity distribution may be the input into the evaluation at 212. Or, the measured radiation intensity variation at the various spatial positions may be subtracted/added to a calculated radiation intensity at the corresponding various spatial positions obtained using, e.g., a numerical Maxwell solver such as 210, to arrive at a corrected computed radiation intensity distribution. So, for example, the computed radiation intensity distribution 208 may be corrected to arrive at a corrected radiation intensity distribution, which corrected radiation intensity distribution may be the input into the evaluation at 212. The computed corrected radiation intensity distribution corrects for variation in gap regardless of the control mechanism used to establish, and maintain, the gap.

At step S105, the corrected radiation intensity distribution may be used in a process to derive one or more parameters of interest of the target. So, as discussed above, the measured radiation intensity distribution 108 or computed radiation intensity distribution 208 may be corrected as described above and used in the process of FIG. 6 as the input to step 212 for the derivation of one or more parameters of interest relating to the target from the measured radiation intensity distribution. So, a corrected radiation distribution may be used to reconstruct one or more parameters of interest associated with the measured target structure.

The aforementioned discussion assumes that only the variation of gap is non-zero. However, this may not always be true. As such, it is likely in some instances that variation in other parameters (e.g., the height of the grating structure, the height of a layer, etc.) is non-zero for the reconstruction. Accordingly, the average radiation intensity change of the pupil for a given pixel with respect to the non-zero parameter(s) of interest may be written as a function of the statistical variance $\mu_2$ of the gap variation distribution as follows:

$$\overline{\Delta I}(\mu_2) = \frac{1}{2}\mu_2 H_{aa} + \sum_{i=1}^{n}\left(\frac{1}{6}\mu_2 T_{aai}\Delta P_i + \sum_{j=1}^{n}\left(\frac{1}{24}\mu_2 Faaij\Delta P_i\Delta P_j + \ldots\right)\right) \qquad \text{Eq. (8)}$$

Thus, if more accuracy is desired for a situation where variation in one or more parameters of interest other than the gap is non-zero, the coefficients $T_{aai}$ of the third-order derivative tensor can be calculated (e.g., only once) to perform an iterative step in which the pupil is corrected using Equation (8) using the reconstructed parameter variation from the first reconstruction (i.e., using Equation (5)), at the computational cost of a second reconstruction. In other words, once a third-order derivative tensor for dependence of radiation intensity on the gap variation for one or more parameters is calculated, a variation in radiation intensity is evaluated for each of the one or more parameters. Thus, this variation in radiation intensity is calculated based on the statistical variance of gap variation distribution, the second-order derivative tensor, the third-order derivative tensor and the variation in the one or more parameters. Thus, a more robust correction for the measured or computed radiation distribution can then be iteratively evaluated to provide a more accurate computed radiation distribution for a more accurate reconstruction of one or more parameters relating to the target. Because the third-order derivative tensor for each of the one or more parameters may need to be computed only once, the computational cost for the second iteration is relatively low.

It is possible to further reduce the computational cost for the two iteration process discussed above by combining the two steps into a single optimization routine (for computing the one or more parameters based on the computed radiation distribution). In such an optimization routine, the pupil is re-corrected in one or more intermediate steps of the first optimization. This will decrease the calculation time, as the second full reconstruction may not be needed.

Figure 15:
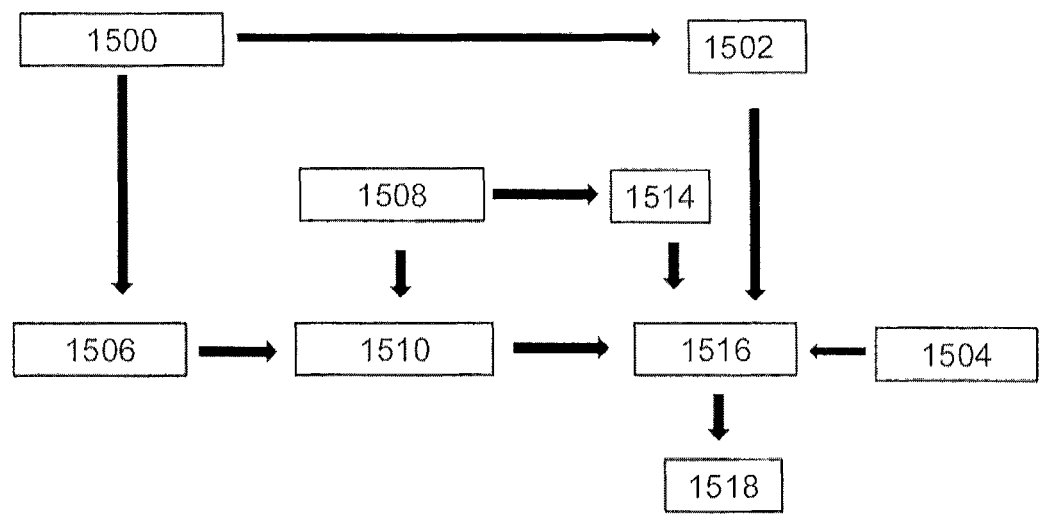
FIG. 15 schematically depicts a flow diagram of a process to derive one or more parameters of interest of a target pattern based on a measured data obtained using a SIL.

FIG. 15 schematically depicts a flow diagram for the correction of intensity distribution and use of the corrected intensity distribution in a process of reconstruction of one or more parameters of a target measured using a SIL. At 1500, a nominal parametric model for the target structure is set up (e.g., with dimensions of one or more layers associated with the target, one or more refractive indices of one or more layers, nominal gap value for measurement, measured radiation wavelength and/or polarization, etc.). At 1502, a second-order derivative tensor (and optionally one or more higher order derivative tensors, e.g. a third-order derivative tensor) for the variation of intensity as a function of the variation of one or more parameters of the model is calculated. See, e.g., equation (3). For example, a second-order derivative tensor for variation of intensity as a function of gap variation may be calculated. At 1506, an ideal pupil (radiation distribution) expected from measuring the target with a measurement beam using the SIL is calculated using the nominal parametric model and is optionally calculated for various gap values.

At 1504, a radiation intensity distribution is measured for the target using the SIL. Further, at 1508, a gap variation distribution is obtained for at least part of the acquisition time used to obtain the measured radiation intensity distribution of 1504. Optionally, at 1510 if ideal pupils were calculated for various gap values at 1506, a modified ideal pupil may be obtained by calculating a weighted average of the pupils based on the ideal pupils at the various gap values obtained at 1506 and the gap variation distribution obtained at 1508. Optionally, the modified ideal pupil may be used in a reconstruction process in place of the computed radiation intensity distribution 208 in FIG. 6. This modified ideal pupil would not include a correction for the variation in gap, but would rather merely provide an account for the variation in the gap in the creation of the modified pupil. At 1514, one or more mathematical moments are calculated from the gap variation distribution. For example, variance of the gap variation distribution may be calculated.

At 1516, a corrected radiation intensity distribution is calculated based on the second (and/or higher) order derivative tensor determined at 1502 and based on the gap variation distribution at 1514. The corrected radiation intensity distribution may be a corrected version of the ideal pupil at 1506, of the modified ideal pupil at 1510 or of the measured radiation intensity distribution of 1504.

At 1518, the correction radiation intensity distribution is applied to a reconstruction process to derive one or more parameters of interest of the target. For example, the process of FIG. 6 may be used at 1518. If the process of FIG. 6 were used, the corrected version of the ideal pupil at 1506 or the modified ideal pupil at 1510 may be substituted for the computed radiation intensity distribution 208. Similarly, if the process of FIG. 6 were used, the corrected version of the measured radiation intensity distribution of 1504 may be substituted for the measured radiation intensity distribution 108.

Thus, in an embodiment, a gap control signal is used to determine the dynamics (and thus distribution) of the gap during an acquisition time to apply this information (e.g., in a feed forward fashion) to the modeling, e.g., reconstruction of a parameter of interest from measured radiation. Further, in an embodiment, the gap variation distribution function is used to model the measured pupil. In an embodiment, the relation between the statistical variance of the gap variation distribution and intensity in the pupil is used to correct a measured or computed pupil for the dynamic residual error in the gap during the measurement. In an embodiment, an iterative model is used to incorporate the effect of parameter variations in the correction of the pupil, making the correction method more robust against model errors.

So, an embodiment may enable decrease in reproducibility error and thus allow for a better precision of a reconstructed parameter of interest. Since an embodiment is based on an algorithmic approach (i.e. a particular way of modeling measured data), it will likely be a cheaper solution than a hardware solution (e.g. an improved mechanical or control system to decrease the gap variation).

While the embodiments disclosed herein use optical metrology as an application of the disclosed technique, the technique can be applied in other applications of SILs used to reconstruct a structure based on radiation captured by SILs, or in any other applications where an object is positioned and/or maintained very close to another object. The technique need not be applied exclusively as described above, and could be applied in combination with one or more other techniques, including one or more techniques discussed in the cited documents.

An embodiment of the invention may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

Any controllers described herein may each or in combination be operable when the one or more computer programs are read by one or more computer processors located within at least one component of the lithographic apparatus. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers may include data storage medium for storing such computer programs, and/or hardware to receive such medium. So the controller(s) may operate according the machine readable instructions of one or more computer programs. Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Further embodiments according to the invention are provided in below numbered clauses:

1. A method involving a radiation intensity distribution for a target measured using an optical component at a gap from the target, the method comprising:
    calculating a correction factor for the variation of radiation intensity of the radiation intensity distribution as a function of variation of the distance of the gap.
2. The method of clause 1, wherein the correction factor comprises a second-order derivative tensor.
3. The method of clause 1 or clause 2, further comprising calculating a variance of a gap variation distribution of the gap during a measurement of the target.
4. The method of any of clauses 1-3, further comprising correcting the radiation intensity distribution based on the correction factor.
5. The method of clause 4, wherein the correcting further comprises correcting the radiation intensity distribution based on a variance of a gap variation distribution of the gap during a measurement of the target.
6. The method of clause 4 or clause 5, further comprising deriving a parameter of interest for the target based on the corrected radiation distribution.
7. The method of any of clauses 4-6, wherein the radiation intensity distribution corrected is a measured radiation intensity distribution.
8. The method of any of clauses 1-7, further comprising:
    for the target structure, calculating a third-order derivative tensor for dependence of the variation in radiation intensity of the radiation intensity distribution on variation of a parameter other than variation of the distance of the gap; and
    determining a variation in radiation intensity as a function of the statistical variance of variation of the distance of the gap during a measurement of the target, a second-order derivative tensor for the variation of radiation intensity of the radiation intensity distribution as a function of variation of the distance of the gap, the third-order derivative tensor and the variation in the parameter.
9. The method of any of clauses 1-8, wherein the optical component comprises a solid immersion lens and the gap is less than or equal to 100 nm.
10. The method of any of clauses 1-9, wherein the gap variation distribution is based on a measured gap signal.
11. The method of any of clauses 1-10, wherein the correction factor comprises a correction for each of a plurality of pixels of the radiation intensity distribution.
12. A method comprising:
    for a given target structure, calculating a second-order derivative tensor for dependence of radiation intensity on a gap between the target structure and an optical element;
    determining a statistical variance of a gap variation distribution over a measurement period; and
    determining a variation in radiation intensity for the target structure based on the statistical variance and the second-order derivative tensor.
13. The method of clause 12, wherein the gap variation distribution is based on a measured gap signal.
14. The method of clause 13, wherein the measured gap signal comprises a gap control signal received from a controller positioning the optical element relative to the target.
15. The method of any of clauses 12-14, wherein the determining further comprises applying the determined variation in radiation intensity to a radiation intensity distribution of the target structure to obtain a corrected radiation intensity distribution for the target structure
16. The method of clause 15, further comprising deriving a parameter associated with the target based on the corrected radiation intensity distribution.
17. The method of any of clauses 12-16, further comprising:

for the target structure, calculating a third-order derivative tensor for dependence of radiation intensity on variation of a parameter other than variation of the distance of the gap; and
wherein determining the variation in radiation intensity is further based on the third-order derivative tensor and the variation in the parameter.
18. The method of any of clauses 12-17, wherein the optical component comprises a solid immersion lens and the gap is less than or equal to 100 nm.
19. A method comprising:
for a given target structure, calculating a second-order derivative tensor for dependence of radiation intensity on a gap between the target structure and an optical element;
evaluating statistical variance of a gap variation distribution for a measurement period of the target, the gap variation distribution being based on a measured gap signal; and
evaluating a mean radiation intensity variation across a pupil as a function of variation of the gap based on the second-order derivative tensor and the statistical variance of the gap variation distribution.
20. A method of manufacturing devices wherein a device pattern is applied to a series of substrates using a lithographic process, the method including inspecting at least a target formed as part of or beside the device pattern on at least one of the substrates using the method of any of clauses 1-19, and controlling the lithographic process for later substrates in accordance with the result of the method.
21. A non-transitory computer program product comprising machine-readable instructions for causing a processor to cause performance of the method of any of clauses 1-19.

Although specific reference may have been made above to the use of embodiments of the invention in the context of optical lithography, it will be appreciated that the invention may be used in other applications, for example imprint lithography, and where the context allows, is not limited to optical lithography. The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:
1. A method involving a radiation intensity distribution for a target measured using an optical component at a gap from the target, the method comprising:
calculating a correction factor for the variation of radiation intensity of the radiation intensity distribution as a function of variation of the distance of the gap, the correction factor configured to correct a measured radiation intensity distribution after it has been measured and/or to correct a radiation intensity distribution that is calculated.
2. The method of claim 1, wherein the correction factor comprises a second-order derivative tensor.
3. The method of claim 1, further comprising calculating a variance of a gap variation distribution of the gap during a measurement of the target.
4. The method of claim 1, further comprising correcting the radiation intensity distribution based on the correction factor.
5. The method of claim 4, wherein the correcting further comprises correcting the radiation intensity distribution based on a variance of a gap variation distribution of the gap during a measurement of the target.
6. The method of claim 4, further comprising deriving a parameter of interest for the target based on the corrected radiation distribution.
7. The method of claim 4, wherein the radiation intensity distribution corrected is a measured radiation intensity distribution.
8. The method of claim 1, further comprising:
for the target structure, calculating a third-order derivative tensor for dependence of the variation in radiation intensity of the radiation intensity distribution on variation of a parameter other than variation of the distance of the gap; and
determining a variation in radiation intensity as a function of: the statistical variance of variation of the distance of the gap during a measurement of the target, a second-order derivative tensor for the variation of radiation intensity of the radiation intensity distribution as a function of variation of the distance of the gap, the third-order derivative tensor and the variation in the parameter.
9. A method, comprising:
for a given target structure, calculating a second-order derivative tensor for dependence of radiation intensity on a gap between the target structure and an optical element;
determining a statistical variance of a gap variation distribution over a measurement period; and
determining a variation in radiation intensity for the target structure based on the statistical variance and the second-order derivative tensor.
10. The method of claim 9, wherein the gap variation distribution is based on a measured gap signal.
11. The method of claim 10, wherein the measured gap signal comprises a gap control signal received from a controller positioning the optical element relative to the target structure.
12. The method of claim 9, wherein the determining further comprises applying the determined variation in radiation intensity to a radiation intensity distribution of the target structure to obtain a corrected radiation intensity distribution for the target structure.
13. The method of claim 12, further comprising deriving a parameter associated with the target structure based on the corrected radiation intensity distribution.

14. The method of claim 9, further comprising:
for the target structure, calculating a third-order derivative tensor for dependence of radiation intensity on variation of a parameter other than variation of the distance of the gap; and
wherein determining the variation in radiation intensity is further based on the third-order derivative tensor and the variation in the parameter.

15. The method of claim 9, wherein the optical component comprises a solid immersion lens and the gap is less than or equal to 100 nm.

16. A method comprising:
for a given target structure, calculating a second-order derivative tensor for dependence of radiation intensity on a gap between the target structure and an optical element;
evaluating statistical variance of a gap variation distribution for a measurement period of the target structure, the gap variation distribution being based on a measured gap signal; and
evaluating a mean radiation intensity variation across a pupil as a function of variation of the gap based on the second-order derivative tensor and the statistical variance of the gap variation distribution.

17. A method of manufacturing devices wherein a device pattern is applied to a series of substrates using a lithographic process, the method including inspecting at least a target formed as part of or beside the device pattern on at least one of the substrates, executing the method of claim 1, and controlling a manufacturing process for later substrates based on the result of the method.

18. A non-transitory computer program product comprising machine-readable instructions for causing a processor to cause performance of a method involving a radiation intensity distribution for a target measured using an optical component at a gap from the target, the method comprising calculating a correction factor for the variation of radiation intensity of the radiation intensity distribution as a function of variation of the distance of the gap, the correction factor configured to correct a measured radiation intensity distribution after it has been measured and/or to correct a radiation intensity distribution that is calculated.

19. A system comprising:
an inspection apparatus configured to provide a beam on a measurement target on a substrate and to detect radiation redirected by the target to determine a parameter of a manufacturing process; and
the non-transitory computer program product of claim 18.

20. The system of claim 19, further comprising a lithographic apparatus, the lithographic apparatus comprising a support structure configured to hold a patterning device to modulate a radiation beam and a projection optical system arranged to project the modulated radiation beam onto a radiation-sensitive substrate.

* * * * *